US012797475B2

(12) United States Patent
Wu et al.

(10) Patent No.: US 12,797,475 B2
(45) Date of Patent: Nov. 17, 2026

(54) CALCIUM-SENSING RECEPTOR AGONIST COMPOUND AND APPLICATION THEREOF

(71) Applicant: BEIJING TUO JIE BIOPHARMACEUTICAL CO. LTD., Beijing (CN)

(72) Inventors: Fangzhou Wu, Beijing (CN); Jin Zhang, Beijing (CN); Fei Gao, Beijing (CN); Ran Wu, Beijing (CN); Cheng Liao, Beijing (CN); Lei Wang, Beijing (CN)

(73) Assignee: BEIJING TUO JIE BIOPHARMACEUTICAL CO. LTD., Beijing (CN)

( * ) Notice: Subject to any disclaimer, the term of this patent is extended or adjusted under 35 U.S.C. 154(b) by 0 days.

(21) Appl. No.: 17/783,233

(22) PCT Filed: Dec. 8, 2020

(86) PCT No.: PCT/CN2020/134598

§ 371 (c)(1),
(2) Date: Jun. 7, 2022

(87) PCT Pub. No.: WO2021/115272

PCT Pub. Date: Jun. 17, 2021

(65) Prior Publication Data

US 2023/0041996 A1 Feb. 9, 2023

(30) Foreign Application Priority Data

Dec. 9, 2019 (CN) ........................ 201911250088.1

(51) Int. Cl.
*A61K 47/54* (2017.01)
*A61P 5/20* (2006.01)

(52) U.S. Cl.
CPC .............. *A61K 47/542* (2017.08); *A61P 5/20* (2018.01)

(58) Field of Classification Search
CPC ................................ A61K 47/542; A61P 5/20
See application file for complete search history.

(56) References Cited

U.S. PATENT DOCUMENTS

2011/0028394 A1* 2/2011 Karim ........................ A61P 3/14 514/21.7
2014/0315809 A1* 10/2014 Walter .................... A61P 19/08 514/11.8

FOREIGN PATENT DOCUMENTS

CN 1741984 A 3/2006
CN 103270018 A 8/2013
CN 103391920 A 11/2013
CN 104168955 A 11/2014
CN 102711789 B 6/2018

OTHER PUBLICATIONS

Souqiyyeh M.Z. et al., Survey of Attitudes of Physicians toward the Current Evaluation and Treatment of Chronic Kidney Disease-Mineral and Bone Disorder (CKD-MBD), Saudi Journal of Kidney Disease and Transplantation, vol. 21, No. 1, pp. 93-101, Dec. 31, 2010 (9 pages).
International Search Report and Written Opinion for International Patent Application No. PCT/CN2020/134598 dated Mar. 10, 2021 (12 pages).

* cited by examiner

*Primary Examiner* — Li N Komatsu
(74) *Attorney, Agent, or Firm* — Morgan, Lewis & Bockius LLP

(57) ABSTRACT

Provided are a calcium-sensing receptor (CaSR) agonist compound and application thereof. Specifically, provided are a series of polypeptide CaSR agonist compounds and pharmaceutically acceptable salts thereof, which have agonist effects on human CaSRs to reduce plasma parathyroid hormone and serum calcium ion levels, and can be used for treatment of metabolic diseases such as primary hyperparathyroidism, secondary hyperparathyroidism, and tumor-induced hypercalcemia.

5 Claims, 4 Drawing Sheets

Specification includes a Sequence Listing.

CALCIUM-SENSING RECEPTOR AGONIST COMPOUND AND APPLICATION THEREOF

CROSS-REFERENCE TO RELATED APPLICATIONS

The present application is the national stage of International Patent Application No. PCT/CN2020/134598, filed on Dec. 8, 2020, which claims the benefit of and priority to Chinese Patent Application No. 201911250088.1 filed on Dec. 9, 2019, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 8, 2020, is named "702126CPUS_126268-5032-US_ST25_Sequence_Listing.TXT" and is approximately 30 kilobytes in size.

TECHNICAL FIELD

The present disclosure relates to the field of biological pharmaceutics, and particularly to a compound having agonist effect on human calcium-sensing receptor (CaSR) or a pharmaceutically acceptable salt thereof, a composition comprising the same, and use thereof in treating metabolic diseases such as primary hyperparathyroidism, secondary hyperparathyroidism, hypercalcemia and other associated metabolic diseases.

BACKGROUND

Secondary hyperparathyroidism refers to a chronic compensated manifestation where in the case of chronic renal insufficiency, intestinal malabsorption syndrome, Fanconi syndrome, renal tubular acidosis, vitamin D deficiency or resistance, pregnancy, lactation and the like, the parathyroid glands are in prolonged stimulation with low serum calcium or magnesium or high serum phosphorus and secrete excessive parathyroid hormone to increase serum calcium and magnesium and to reduce serum phosphorus, and that is usually accompanied by hyperplasia in the parathyroid glands. Prolonged parathyroid hyperplasia eventually leads to the genesis of functionally autonomous adenomas.

Calcium-sensing receptor (CaSR) refers to a G-protein coupled receptor (GPCR) family A member distributed on the cell surface in human parathyroid glands. Secretion of parathyroid hormone is highly regulated by calcium-sensing receptor on parathyroid cell surface to maintain the steady levels of minerals in human body. The calcium-sensing receptor continuously monitors subtle changes in calcium ion concentration in human body and responds accordingly by altering the level of parathyroid hormone secretion.

In patients with chronic kidney disease, the need of steady levels of calcium and phosphorus ions in the body results in the continuous secretion of parathyroid hormone in the parathyroid glands. This continuous secretion of parathyroid hormone is initially adaptive, but will eventually lead to hyperplasia in the parathyroid glands and excessive parathyroid hormone in the body and induce secondary hyperparathyroidism as chronic kidney disease progresses. Studies have shown that persistent secondary hyperparathyroidism will lead to the loss of calcium-sensing receptor and vitamin D receptor on parathyroid cell surface. These downstream pathological effects caused by the disease further lead to dysregulation of the steady mineral levels by the parathyroid glands.

Calcimimetics generally refer to compounds that have similar physiological functions and mechanisms of action to calcium ion and can directly activate calcium-sensing receptor on parathyroid cell surface. Cinacalcet hydrochloride, an organic small-molecule calcimimetic developed by Amgen, can activate calcium-sensing receptor on parathyroid cell surface and inhibit the secretion of parathyroid hormone, thus achieving goals of treating associated metabolic diseases such as secondary hyperparathyroidism. Cinacalcet hydrochloride has been approved for the treatment of secondary hyperparathyroidism in chronic kidney disease patients receiving dialysis, and is administered orally one to two times daily with a dose up to 90 mg. Cinacalcet hydrochloride shows clinically excellent efficacy in reducing plasma parathyroid hormone levels in patients with secondary hyperparathyroidism. However, remarkable drug-induced adverse effects such as nausea, vomiting and diarrhea associated with gastrointestinal adverse effects are observed during the treatment. In addition, the oral administration of cinacalcet hydrochloride imposes great burden in chronic kidney disease patients receiving dialysis, and cinacalcet hydrochloride has been demonstrated to inhibit cytochrome 450 and induce associated drug-drug interaction. Such adverse effects associated with the use of cinacalcet hydrochloride reduce patient adherence and compliance to some extent.

Therefore, a calcium-sensing receptor agonist compound that can be intravenously administered and can reduce the secretion of parathyroid hormone by activating calcium-sensing receptor on parathyroid cell surface to achieve the therapeutic purpose of treating associated metabolic diseases such as secondary hyperparathyroidism is desirable. Such calcium-sensing receptor agonist compounds can significantly improve the treatment adherence and compliance in patients with chronic kidney disease.

SUMMARY

The present disclosure is intended to provide a compound consisting of a peptide and a conjugated group or a pharmaceutically acceptable salt thereof, wherein the peptide consists of an amino acid sequence of formula (I):

(I) (SEQ ID NO: 39)

$$X_1\text{-}X_2\text{-}X_3\text{-}X_4\text{-}X_5\text{-}X_6\text{-}X_7$$

wherein:

$X_1$ is D-Cys;

$X_2$ is selected from the group consisting of D-Phg, D-Phe(4-$CH_3$), D-Phe(2-Cl), D-Tyr, D-Trp, D-Ser, D-Arg, D-Trp and D-His;

$X_3$ is D-Arg;

$X_4$ is selected from the group consisting of D-Arg, D-Phg, D-Phe(4-$CH_3$), D-2-Thi, D-Phe(4-$NO_2$), D-2-Nal, D-hPhe, D-Abu, D-Tle, D-hLeu, D-Cha, D-Ser, D-Gln, D-Tyr, D-Ile, D-Ser, D-His, D-Val and D-Chg;

$X_5$ is D-Arg;

$X_6$ is selected from the group consisting of D-Ala, D-Abu, D-Ser and Gly;

$X_7$ is D-Arg;

wherein the peptide and the conjugated group are covalently linked by a disulfide bond; wherein the conjugated group is L-Cys and the $X_1$ residue of the peptide is covalently linked to the conjugated group by a disulfide bond;

and the N-terminal $X_1$ of the peptide is acetylated and the C-terminal $X_7$ of the peptide is amidated.

In one embodiment, for the compound or the pharmaceutically acceptable salt thereof as described above, in the peptide of formula (I):

$X_1$ is D-Cys;

$X_2$ is selected from the group consisting of D-Phg, D-Phe(4-$CH_3$), D-Phe(2-Cl), D-Tyr, D-Trp, D-Ser and D-His;

$X_3$ is D-Arg;

$X_4$ is D-Arg;

$X_5$ is D-Arg;

$X_6$ is selected from the group consisting of D-Ala, D-Abu, D-Ser and Gly;

$X_7$ is D-Arg;

wherein the peptide and the conjugated group are covalently linked by a disulfide bond;

wherein the conjugated group is L-Cys and the $X_1$ residue of the peptide is covalently linked to the conjugated group by a disulfide bond;

and the N-terminal $X_1$ of the peptide is acetylated and the C-terminal $X_7$ of the peptide is amidated.

In another embodiment, for the compound or the pharmaceutically acceptable salt thereof as described above, in the peptide of formula (I):

$X_1$ is D-Cys;

$X_2$ is D-Arg;

$X_3$ is D-Arg;

$X_4$ is selected from the group consisting of D-Arg, D-Phg, D-Phe(4-$CH_3$), D-2-Thi, D-Phe(4-$NO_2$), D-2-Nal, D-hPhe, D-Abu, D-Tle, D-hLeu, D-Chg, D-Ser, D-Cha, D-Gln, D-Tyr, D-His and D-Val;

$X_5$ is D-Arg;

$X_6$ is selected from the group consisting of D-Ala, D-Abu, D-Ser and Gly;

$X_7$ is D-Arg;

wherein the peptide and the conjugated group are covalently linked by a disulfide bond;

wherein the conjugated group is L-Cys and the $X_1$ residue of the peptide is linked to the conjugated group by a disulfide bond;

and the N-terminal $X_1$ of the peptide is acetylated and the C-terminal $X_7$ of the peptide is amidated.

In another embodiment, for the compound or the pharmaceutically acceptable salt thereof as described above, in the peptide of formula (I):

$X_1$ is D-Cys;

$X_2$ is D-Arg;

$X_3$ is D-Arg;

$X_4$ is selected from the group consisting of D-Phg, D-Phe(4-$CH_3$), D-2-Thi, D-Phe(4-$NO_2$), D-2NaI, D-hPhe, D-Abu, D-Tle, D-hLeu, D-Chg, D-Ser, D-Cha, D-Gln, D-Tyr, D-Ile, D-His and D-Val;

$X_5$ is D-Arg;

$X_6$ is selected from the group consisting of D-Ala, D-Abu, D-Ser and Gly;

$X_7$ is D-Arg;

wherein the peptide and the conjugated group are covalently linked by a disulfide bond;

wherein the conjugated group is L-Cys and the $X_1$ residue of the peptide is linked to the conjugated group by a disulfide bond;

and the N-terminal $X_1$ of the peptide is acetylated and the C-terminal $X_7$ of the peptide is amidated.

In another embodiment, for the compound or the pharmaceutically acceptable salt thereof as described above, in the peptide of formula (I):

$X_1$ is D-Cys;

$X_2$ is D-Arg;

$X_3$ is D-Arg;

$X_4$ is selected from the group consisting of D-Phe(4-$CH_3$), D-2-Thi, D-Abu, D-hLeu and D-Val;

$X_5$ is D-Arg;

$X_6$ is selected from the group consisting of D-Ala and D-Ser;

$X_7$ is D-Arg;

wherein the conjugated group is L-Cys and the $X_1$ residue of the peptide is covalently linked to the conjugated group by a disulfide bond;

and the N-terminal $X_1$ of the peptide is acetylated and the C-terminal $X_7$ of the peptide is amidated.

In some embodiments, $X_4$ is selected from the group consisting of D-Abu and D-Val; in some other embodiments, $X_4$ is D-Abu.

The present disclosure further provides a compound of formula (II) or a pharmaceutically acceptable salt thereof, wherein the two ends are linked as follows:

$$R1\text{-}X_1\text{-}X_2\text{-}X_3\text{-}X_4\text{-}X_5\text{-}X_6\text{-}X_7\text{-}R2 \quad \text{(II)}$$

wherein:

R1 is H, alkyl, acetyl, formyl, benzoyl, trifluoroacetyl, D-pGlu or L-pGlu;

R2 is —$NH_2$ or —OH;

$X_1$, $X_2$, $X_3$, $X_4$, $X_5$, $X_6$ and $X_7$ are as defined for formula (I) above.

In one embodiment, for the compound of formula (II) or the pharmaceutically acceptable salt thereof:

R1 is acetyl; $X_1$ is amino acid residue D-Cys; $X_2$ is selected from the group consisting of amino acid residues D-Phg, D-Phe(4-$CH_3$), D-Phe(2-Cl), D-Tyr, D-Trp, D-Ser, D-Arg and D-His; $X_3$ is amino acid residue D-Arg; $X_4$ is selected from the group consisting of D-Arg, D-Phg, D-Phe(4-$CH_3$), D-2-Thi, D-Phe(4-$NO_2$), D-2-NaI, D-hPhe, D-Abu, D-Tle, D-hLeu, D-Cha, D-Ser, D-Gln, D-Tyr, D-Ile, D-Ser, D-His, D-Val and D-Chg; $X_5$ is amino acid residue D-Arg; $X_6$ is selected from the group consisting of amino acid residues D-Ala, D-Abu, D-Ser and Gly; $X_7$ is amino acid residue D-Arg; and R2 is —$NH_2$.

In one embodiment, for the compound of formula (II) or the pharmaceutically acceptable salt thereof: R1 is acetyl; $X_1$ is amino acid residue D-Cys; $X_2$ is selected from the group consisting of amino acid residues D-Phg, D-Phe(4-$CH_3$), D-Phe(2-Cl), D-Tyr, D-Trp, D-Ser and D-His; $X_3$ is amino acid residue D-Arg; $X_4$ is amino acid residue D-Arg; $X_5$ is amino acid residue D-Arg; $X_6$ is selected from the group consisting of amino acid residues D-Ala, D-Abu, D-Ser and Gly; $X_7$ is amino acid residue D-Arg; and R2 is —$NH_2$.

In one embodiment, for the compound of formula (II) or the pharmaceutically acceptable salt thereof: R1 is acetyl; $X_1$ is amino acid residue D-Cys; $X_2$ is amino acid residue D-Arg; $X_3$ is amino acid residue D-Arg; $X_4$ is selected from the group consisting of amino acid residues D-Arg, D-Phg, D-Phe(4-$CH_3$), D-2-Thi, D-Phe(4-$NO_2$), D-2NaI, D-hPhe, D-Abu, D-Tle, D-hLeu, D-Chg, D-Ser, D-Cha, D-Gln, D-Tyr, D-His and D-Val; $X_5$ is amino acid residue D-Arg; $X_6$ is selected from the group consisting of amino acid residues D-Ala, D-Abu, D-Ser and Gly; $X_7$ is amino acid residue D-Arg; and R2 is —$NH_2$.

In one embodiment, for the compound of formula (II) or the pharmaceutically acceptable salt thereof: R1 is acetyl; $X_1$ is amino acid residue D-Cys; $X_2$ is amino acid residue D-Arg; $X_3$ is amino acid residue D-Arg; $X_4$ is selected from the group consisting of amino acid residues D-Phg, D-Phe(4-$CH_3$), D-2-Thi, D-Phe(4-$NO_2$), D-2NaI, D-hPhe, D-Abu, D-Tle, D-hLeu, D-Chg, D-Ser, D-Cha, D-Gln, D-Tyr, D-Ile, D-His and D-Val; $X_5$ is amino acid residue D-Arg; $X_6$ is selected from the group consisting of amino acid residues D-Ala, D-Abu, D-Ser and Gly; $X_7$ is amino acid residue D-Arg; and R2 is —$NH_2$.

In one embodiment, for the compound of formula (I) or (II) or the pharmaceutically acceptable salt thereof, when $X_1$ is amino acid residue D-Cys, the $X_1$ residue links to a second thiol group through a side chain disulfide bond.

In one embodiment, the compound or the pharmaceutically acceptable salt thereof is selected from the group consisting of the following compounds:

| Compound | Sequence | SEQ ID NO: |
|---|---|---|
| 1 | Ac-c(C)-(D-Phg)-r-r-r-a-r-$NH_2$ | 1 |
| 2 | Ac-c(C)-[D-Phe(2-Cl)]-r-r-r-a-r-$NH_2$ | 2 |
| 3 | Ac-c(C)-[D-Phe(4-$CH_3$)]-r-r-r-a-r-$NH_2$ | 3 |
| 4 | Ac-c(C)-(D-Tyr)-r-r-r-a-r-$NH_2$ | 4 |
| 5 | Ac-c(C)-(D-Trp)-r-r-r-a-r-$NH_2$ | 5 |
| 6 | Ac-c(C)-s-r-r-r-s-r-$NH_2$ | 6 |
| 7 | Ac-c(C)-h-r-r-r-G-r-$NH_2$ | 7 |
| 8 | Ac-c(C)-s-r-r-r-G-r-$NH_2$ | 8 |
| 9 | Ac-c(C)-w-r-r-r-G-r-$NH_2$ | 9 |
| 10 | Ac-c(C)-h-r-r-r-s-r-$NH_2$ | 10 |
| 11 | Ac-c(C)-r-r-(D-Phg)-r-a-r-$NH_2$ | 11 |
| 12 | Ac-c(C)-r-r-[D-Phe(4-$CH_3$)]-r-a-r-$NH_2$ | 12 |
| 13 | Ac-c(C)-r-r-(D-2-Thi)-r-a-r-$NH_2$ | 13 |
| 14 | Ac-c(C)-r-r-[D-Phe(4-$NO_2$)]-r-a-r-$NH_2$ | 14 |
| 15 | Ac-c(C)-r-r-(D-2-NaI)-r-a-r-$NH_2$ | 15 |
| 16 | Ac-c(C)-r-r-(D-hPhe)-r-a-r-$NH_2$ | 16 |
| 17 | Ac-c(C)-r-r-(D-Abu)-r-a-r-$NH_2$ | 17 |
| 18 | Ac-c(C)-r-r-(D-Tle)-r-a-r-$NH_2$ | 18 |
| 19 | Ac-c(C)-r-r-(D-hLeu)-r-a-r-$NH_2$ | 19 |
| 20 | Ac-c(C)-r-r-(D-Chg)-r-a-r-$NH_2$ | 20 |
| 21 | Ac-c(C)-r-r-(D-Cha)-r-a-r-$NH_2$ | 21 |
| 22 | Ac-c(C)-r-r-s-r-G-r-$NH_2$ | 22 |
| 23 | Ac-c(C)-r-r-q-r-G-r-$NH_2$ | 23 |
| 24 | Ac-c(C)-r-r-y-r-a-r-$NH_2$ | 24 |
| 25 | Ac-c(C)-r-r-s-r-s-r-$NH_2$ | 25 |

-continued

| Compound | Sequence | SEQ ID NO: |
|---|---|---|
| 26 | Ac-c(C)-r-r-q-r-s-r-$NH_2$ | 26 |
| 27 | Ac-c(C)-r-r-h-r-s-r-$NH_2$ | 27 |
| 28 | Ac-c(C)-r-r-h-r-G-r-$NH_2$ | 28 |
| 29 | Ac-c(C)-r-r-v-r-s-r-$NH_2$ | 29 |
| 30 | Ac-c(C)-r-r-v-r-G-r-$NH_2$ | 30 |
| 31 | Ac-c(C)-r-r-(D-Abu)-r-s-r-$NH_2$ | 31 |
| 32 | Ac-c(C)-r-r-(D-Abu)-r-G-r-$NH_2$ | 32 |
| 33 | Ac-c(C)-r-r-(D-hLeu)-r-s-r-$NH_2$ | 33 |
| 34 | Ac-c(C)-r-r-(D-hLeu)-r-G-r-$NH_2$ | 34 |
| 35 | Ac-c(C)-r-r-(D-Chg)-r-s-r-$NH_2$ | 35 |
| 36 | Ac-c(C)-r-r-(D-Chg)-r-G-r-$NH_2$ | 36 |
| 37 | Ac-c(C)-r-r-(D-Tle)-r-s-r-$NH_2$ | 37 |
| 38 | Ac-c(C)-r-r-(D-Tle)-r-G-r-$NH_2$ | 38 |

In the structural formulas of the above table, "Ac-c(C)" denotes that an acetylated cysteine in D configuration (c) at the amino terminus is linked to another cysteine in L configuration (C) by a disulfide bond; "r-$NH_2$" denotes an amidated arginine in the D configuration (r) at the carboxyl terminus.

The present disclosure further provides a pharmaceutical composition comprising any of the aforementioned compounds or the pharmaceutically acceptable salts thereof, and a pharmaceutically acceptable carrier.

The present disclosure further provides use of any of the aforementioned compounds or the pharmaceutically acceptable salts thereof, and the compositions thereof, in preparing a medicament for reducing parathyroid hormone levels in a subject or for treating secondary hyperparathyroidism or tumor-induced hypercalcemia.

The polypeptide compounds disclosed herein are zwitterionic compounds and can be reacted with acidic or basic compounds to form salts by techniques well known to those skilled in the art.

The pharmaceutical composition comprising the polypeptide compound disclosed herein may be used for treating patients in need of such treatment by parenteral administration. For the parenteral routes of administration, subcutaneous injection, intramuscular injection or intravenous injection may be selected. The polypeptide compound disclosed herein may also be administered by transdermal routes, e.g., via a patch on the scalp, optionally an iontophoretic patch; or by transmucosal routes. Such pharmaceutical compositions and preparation methods are well known in the art, and the preferred route of administration is intravenous injection.

The polypeptide compound disclosed herein was prepared by solid-phase synthesis, using a synthesis carrier Rink-amide-MBHA resin (Sunresin, Xi'an). The a amino groups of the amino acid derivatives used in the synthesis process were protected by Fmoc (fluorenylmethyloxycarbonyl) group, and for the side chains of the amino acids the following protecting groups were selected according to functional groups: cysteine side chain thiol, glutamine side chain amino and histidine side chain imidazolyl were protected by Trt (triphenylmethyl), arginine side chain guanidinyl was protected by Pbf (2,2,4,6,7-pentamethyldihydrobenzofuran-5-sulfonyl), tryptophan side chain indolyl was protected by Boc (tert-butyloxycarbonyl), and tyrosine side chain phenolyl and serine side chain hydroxyl were protected by t-Bu (tert-butyl). In the synthesis process, the carboxyl of the C-terminal amino acid residue of the polypeptide was firstly condensed to insoluble Rink-amide MBHA polymer resin in the form of an amide bond, then the Fmoc protecting group on the a amino group was removed using a 25% solution of 4-methylpiperidine in N,N-dimethylformamide (DMF), and then the solid phase carrier and the next amino acid derivative in the sequence were condensed in the excess condition to form an amide bond so as to extend the peptide chain. The procedures of condensation→washing→deprotection→washing→the next round of amino acid condensation were repeated to reach the desired length of the polypeptide chain. Finally a mixed solution of trifluoroacetic acid:water:triisopropylsilane=90:5:5 (v:v:v) was reacted with the resin to cleave the polypeptide from the solid phase carrier, and the mixture was precipitated using frozen methyl tert-butyl ether to obtain a solid crude product of the polypeptide compound. The polypeptide solid crude product was dissolved in a 0.1% solution of trifluoroacetic acid in acetonitrile/water, and purified and separated by a C-18 reverse phase preparative chromatographic column to obtain a purified product of the polypeptide compound.

DETAILED DESCRIPTION OF THE INVENTION

Unless otherwise stated, the terms used in the claims and specification have the following meanings.

The amino acid sequences described herein are represented using the standard one- or three-letter codes for twenty amino acids. Unless otherwise stated, in the present disclosure amino acids in D configuration are represented by the prefix "D-" prior to the standard three-letter codes, e.g., D-Ser, or by the corresponding one-letter codes in lower case, e.g., s; amino acids in L configuration are indicated by the prefix "L-" prior to the standard three-letter codes, e.g., L-Cys, or by the corresponding one-letter codes in upper case, e.g., C; as an exception, glycine is achiral, and is denoted by "Gly" or by the corresponding uppercase single-letter code "G".

The term agonist is defined as a substance that activates the receptors in discussion.

The term calcium-sensing receptor agonist as used in the context herein refers to a substance or ligand that can activate calcium-sensing receptor. As used herein, the term treatment includes inhibiting, alleviating, stopping or reversing the progression or severity of an existing symptom or condition.

Parathyroid hormone, as used herein, is a peptide of 84 amino acids produced by parathyroid glands and its breakdown products. In addition to the full-length parathyroid hormone, various parathyroid hormone fragments that are produced by proteolysis and other metabolic pathways are present in the blood. In the intact parathyroid hormone molecule, the region of residues 1-34 at the amino terminus carries the biological activity. Various methods for measuring parathyroid hormone levels have been developed and are known in the art.

"Natural amino acids" refer to the 20 naturally occurring conventional amino acids, i.e., alanine (Ala, A), cysteine (Cys, C), aspartic acid (Asp, D), glutamic acid (Glu, E), phenylalanine (Phe, F), glycine (Gly, G), histidine (His, H), isoleucine (Ile, I), lysine (Lys, K), leucine (Leu, L), methionine (Met, M), asparagine (Asn, N), proline (Pro, P), glutamine (Gln, Q), arginine (Arg, R), serine (Ser, S), threonine (Thr, T), valine (Val, V), tryptophan (Trp, W) and tyrosine (Tyr, Y).

"Non-natural amino acids" refer to amino acids that are not naturally encoded or found in the genetic codon of any organism. They may be, for example, completely synthetic compounds. Examples include, but are not limited to, D-2-aminobutyric acid (D-Abu), 3-cyclohexyl-D-alanine (D-Cha), 3-(2-thienyl)-D-alanine (D-2-Thi), 2-naphthyl-D-alanine (D-2-Nal), D-phenylglycine (D-Phg), D-2-chlorophenylalanine (D-Phe(2-Cl)), D-4-nitrophenylalanine (D-Phe(4-$NO_2$)), D-4-methylphenylalanine (D-Phe(4-Me)), D-homophenylalanine (D-hPhe), D-tert-leucine (D-Tle), D-homoleucine (D-hLeu), and D-cyclohexylglycine (D-Chg).

Furthermore, it is also included that the C-terminal carboxyl, N-terminal amino and/or side chain functional group of a natural amino acid or a non-natural amino acid is chemically modified.

Descriptions "X is selected from the group consisting of A, B or C", "X is selected from the group consisting of A, B and C", "X is A, B or C", "X is A, B and C" and the like all carry the same meaning, i.e., X may be any one or more of A, B and C.

All hydrogen atoms described in the present disclosure may be replaced by isotope deuterium, and any hydrogen atom in the compounds of the examples to which the present disclosure relates may also be replaced by a deuterium atom.

The term "optional" or "optionally" means that the event or circumstance subsequently described may, but not necessarily, occur, and that the description includes instances where the event or circumstance occurs or does not occur. For example, "a heterocyclyl group optionally substituted with alkyl" means that alkyl may be, but not necessarily, present, and that the description includes instances where the heterocyclyl group is or is not substituted with alkyl.

The term "substituted" means that one or more, preferably up to 5, more preferably 1 to 3 hydrogen atoms in the group are independently substituted with a corresponding number of substituents. It goes without saying that a substituent is only in its possible chemical position, and those skilled in the art will be able to determine (experimentally or theoretically) possible or impossible substitution without undue efforts. For example, it may be unstable when an amino or hydroxy group having a free hydrogen is bound to a carbon atom having an unsaturated (e.g., olefinic) bond.

The term "pharmaceutical composition" refers to a mixture containing one or more of the compounds described herein or a physiologically/pharmaceutically acceptable salt or pro-drug thereof, and other chemical components, for example physiologically/pharmaceutically acceptable carriers and excipients. The pharmaceutical composition is intended to promote the administration to an organism and facilitate the absorption of the active ingredient, thereby exerting biological activities.

The term "pharmaceutically acceptable salt" refers to salts of the disclosed compounds which are safe and effective for use in the body of a mammal and possess the requisite biological activities.

As used herein, a subject refers to a human subject or an animal subject.

As used herein, any group or moiety containing thiol refers to a functional group that contains a sulfur-hydrogen bond and is capable of forming a disulfide bond with another thiol under physiological conditions.

DETAILED DESCRIPTION

Figure 1:
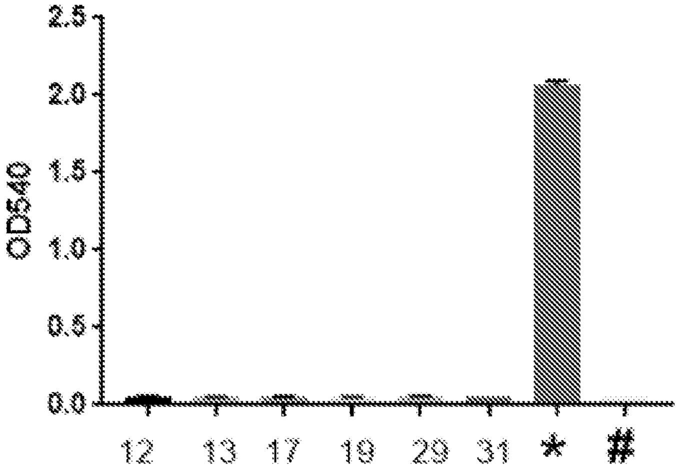
FIG. 1 shows the hemolytic effect of example compounds 12, 13, 17, 19, 29 and 31 against human red blood cells in vitro, wherein * denotes positive control (polyethylene glycol octyl phenyl ether) and #denotes PBS buffer.

The following specific embodiments are provided herein only for illustrating the present disclosure in more detail, rather than limiting the present disclosure.

1. Reagents

| No. | Reagent | Source |
|---|---|---|
| 1 | Rink-amide MBHA resin | Sunresin, Xi'an |
| 2 | O-(1H-6-chlorobenzotriazole-1-yl)-1,1,3,3-tetramethyluronium hexafluorophosphate (HCTU) | Highfine Biotech, Suzhou |
| 3 | 4-Methylmorpholine | TCI Chemicals |
| 4 | Acetonitrile (chromatographic grade) | Sigma-Aldrich |
| 5 | N,N-dimethyl formamide | Sinopharm Chemical Reagent |
| 6 | Dichloromethane | Sinopharm Chemical Reagent |
| 7 | Trifluoroacetic acid | TCI Chemicals |
| 8 | Triisopropylsilane | TCI Chemicals |
| 9 | Methyl tert-butyl ether | TCI Chemicals |
| 10 | 4-Methylpiperidine | TCI Chemicals |
| 11 | L-cysteine | Sigma-Aldrich |
| 12 | Fmoc-D-Cys(Trt)-OH | GL Biochem |
| 13 | Fmoc-D-Arg(Pbf)-OH | GL Biochem |
| 14 | Fmoc-D-Ala-OH | GL Biochem |
| 15 | Fmoc-D-Abu-OH | GL Biochem |
| 16 | Fmoc-D-Phg-OH | GL Biochem |
| 17 | Fmoc-D-Phe(4-$CH_3$)-OH | GL Biochem |
| 18 | Fmoc-D-2-Thi-OH | GL Biochem |
| 19 | Fmoc-D-Phe(4-$NO_2$)-OH | GL Biochem |
| 20 | Fmoc-D-2NaI-OH | GL Biochem |
| 21 | Fmoc-D-hPhe-OH | GL Biochem |
| 22 | Fmoc-D-Tle-OH | GL Biochem |
| 23 | Fmoc-D-hLeu-OH | GL Biochem |
| 24 | Fmoc-D-Chg-OH | GL Biochem |
| 25 | Fmoc-D-Ser(tBu)-OH | GL Biochem |
| 26 | Fmoc-D-Cha-OH | GL Biochem |
| 27 | Fmoc-D-Gln(Trt)-OH | GL Biochem |
| 28 | Fmoc-Gly-OH | GL Biochem |
| 29 | Fmoc-D-Tyr(tBu)-OH | GL Biochem |
| 30 | Fmoc-D-His(Boc)-OH | GL Biochem |
| 31 | Fmoc-D-Val-OH | GL Biochem |
| 32 | Fmoc-D-Phe(2-Cl)-OH | GL Biochem |
| 33 | Fmoc-D-Trp(Boc)-OH | GL Biochem |
| 34 | 2,2'-Dipyridyldisulfide | GL Biochem |

2. Instruments

| No. | Instruments | Source |
|---|---|---|
| 1 | Prelude-X multichannel polypeptide synthesizer | Protein Technology |
| 2 | H-CLASS analytical ultra-performance liquid chromatography | Waters |
| 3 | Xevo liquid chromatography/mass spectrometry | Waters |
| 4 | Labconco multifunctional freeze dryer | Thermo-Fisher Scientific |
| 5 | Prep 150 preparative high performance liquid chromatography | Waters |
| 6 | Multichannel high-speed centrifuge | Sigma |

3. Examples

3.1 Chemical Synthesis of Compound 1

Solid phase peptide synthesis was performed on a Prelude-X automatic polypeptide synthesizer using the Fmoc/tBu synthesis strategy starting from Rink-amide MBHA resin (0.1 mmol). Coupling was performed using 10 equivalents of amino acid residues activated with HCTU and 4-methylmorpholine (the molar ratio of HCTU:4-methylmorpholine:amino acid residues was 1:2:1) in N,N-dimethylformamide at room temperature for 25 min.

After completion of the above peptide-resin synthesis, in a solution of 90:5:5 (v/v/v) trifluoroacetic acid:triisopropylsilane:water and 2,2'-dipyridyldisulfide (1 mmol) at room temperature, cleavage of polypeptide from solid phase resin, removal of side chain protecting group and activation of D-Cys side chain thiol group were synchronously accomplished in 2 h. After the reaction was completed, the mixture was filtered and the resin was washed for 2 times by using trifluoroacetic acid. The filtrates were combined before a large amount of frozen methyl tert-butyl ether was added to precipitate a solid. The mixture was centrifuged and the supernatant was discarded to obtain a crude product of the polypeptide, which was then dried and weighed.

The crude polypeptide obtained above and L-Cys (0.1 mmol) were dissolved in PBS buffer (pH=7.4) and reacted with shaking at room temperature. The production of compound 1 was monitored by ultra-performance liquid chromatography. After completion of the reaction, trifluoroacetic acid (300 μL) was added to the mixture to quench the reaction and for subsequent purification.

The mixture obtained above was filtered through a 0.22 μm membrane and separated by a Waters Prep150 preparative reverse-phase high performance liquid chromatography system with buffers A (0.1% trifluoroacetic acid, aqueous solution) and B (0.1% trifluoroacetic acid, 90% acetonitrile, aqueous solution). The preparative chromatographic column was an X-SELECT OBD C-18 (Waters) reversed-phase chromatographic column, the detection wavelength of a chromatograph was set as 220 nm in the purification process, and the flow rate was 15 mL/min. The purified polypeptide product of compound 1 was obtained after the relevant fractions were collected and lyophilized (45% yield). The purity and the compound identity of the pure polypeptide product were determined by analytical ultra-performance liquid chromatography and ultra-performance liquid chromatography/mass spectrometry, wherein the purity of the compound was 96.78%, and the molecular weight of the compound was 1109.60.

3.2 Chemical Synthesis of Compounds 2-38

Compounds 2-38 of the present disclosure were synthesized using synthetic protocols similar to that of compound 1 and the purity and molecular weight of the synthesized polypeptides were determined by analytical ultra-performance liquid chromatography and ultra-performance liquid chromatography/mass spectrometry, as detailed in Table 1 below:

TABLE 1

Purity and measured molecular weight of the synthesized compounds

| Compound | Purity | Molecular weight |
|---|---|---|
| 2 | 96.00% | 1157.80 |
| 3 | 97.80% | 1137.80 |
| 4 | 95.25% | 1140.00 |
| 5 | 97.72% | 1162.80 |
| 6 | 96.58% | 1079.80 |
| 7 | 98.62% | 1100.00 |
| 8 | 95.20% | 1050.00 |
| 9 | 98.20% | 1149.00 |
| 10 | 95.56% | 1130.00 |
| 11 | 95.69% | 1110.00 |
| 12 | 95.88% | 1138.20 |
| 13 | 99.04% | 1129.60 |
| 14 | 97.64% | 1169.00 |
| 15 | 95.48% | 1174.00 |
| 16 | 97.07% | 1138.20 |
| 17 | 95.79% | 1062.00 |
| 18 | 96.65% | 1090.80 |
| 19 | 96.33% | 1104.40 |
| 20 | 96.82% | 1116.80 |
| 21 | 98.39% | 1130.00 |
| 22 | 96.97% | 1050.00 |
| 23 | 95.47% | 1091.00 |
| 24 | 96.35% | 1140.00 |
| 25 | 95.83% | 1080.00 |
| 26 | 96.92% | 1120.90 |
| 27 | 95.80% | 1130.00 |
| 28 | 96.74% | 1100.20 |
| 29 | 96.56% | 1092.20 |

TABLE 1-continued

Purity and measured molecular weight of the synthesized compounds

| Compound | Purity | Molecular weight |
|---|---|---|
| 30 | 95.98% | 1062.00 |
| 31 | 95.81% | 1077.80 |
| 32 | 99.68% | 1047.80 |
| 33 | 96.03% | 1119.80 |
| 34 | 96.73% | 1090.00 |
| 35 | 98.53% | 1132.00 |
| 36 | 95.25% | 1102.00 |
| 37 | 96.83% | 1106.00 |
| 38 | 96.76% | 1075.80 |

Biological Evaluation

The present disclosure is further illustrated in conjunction with the specific examples, which, however, are not intended to limit the scope of the present disclosure.

1. Reagent for In Vitro and In Vivo Biological Evaluation

| No. | Reagent | Source |
|---|---|---|
| 1 | FBS, 500 mL | ThermoFisher Scientific |
| 2 | DMEM, High Glucose, GlutaMAX, 500 mL | ThermoFisher Scientific |
| 3 | Penicilin-Streptomyces, Liquid, 100 mL (100×) | ThermoFisher Scientific |
| 4 | 1× PBS pH 7.2-7.4 (500 mL) | Solarbio |
| 5 | 1× TrypLE Express Enzyme, no phenol red (500 mL) | ThermoFisher Scientific |
| 6 | Hygromycin B Gold solution (5 g, 1 × 50 mL,1 00 mg/mL) | Invivogen |
| 7 | HEPES, 1M | Gibco |
| 8 | $MgCl_2$, 1M | Sigma-Aldrich |
| 9 | KCl, 1M | Sigma-Aldrich |
| 10 | NaCl, 5M | Sigma-Aldrich |
| 11 | Glucose | Sigma-Aldrich |
| 12 | LiCl, 8M | Sigma-Aldrich |
| 13 | $CaCl_2$, 1M | Sigma-Aldrich |
| 14 | IP-One-Gq Kit (1,000 tests) | Cisbio |

2. Instruments

| No. | Instruments | Source |
|---|---|---|
| 1 | EnVision detector | Perkin Elmer |

3. Test Examples 3.1 Evaluation of Agonist Activity of Compounds 1-38 on Human Calcium-Sensing Receptor (CaSR)

3.1.1 Objective:

The test example is intended to measure the agonist activity of compounds 1-38 on the human calcium-sensing receptor (CaSR).

3.1.2 Procedures:

Stably transfected HEK293/CaSR cells (source: Pharmaron) were cultured in a complete medium (composition: DMEM, high glucose+10% FBS+2 mM GlutaMAX+1× Penicillin-Streptomycin+200 μg/mL Hygromycin B) and incubated at 37° C./5% $CO_2$ till 70%-90% cell confluence.

The cells were digested with TrypLE, inoculated into 384-well cell culture plates, and cultured overnight at 37° C./5% $CO_2$. After buffer exchange, stimulation buffer (HEPES 10 mM, $MgCl_2$ 0.5 mM, KCl 4.2 mM, NaCl 146 mM, glucose 5.5 mM, LiCl 50 mM, $CaCl_2$ 1.2 mM) and various concentrations of the test example compounds were added and incubated at 37° C. for 60 min. Production of IP-One in cells was detected according to the procedures in the Cisbio IP-One Tb kit instructions. The $EC_{50}$ values of various test example compounds in influencing human calcium-sensing receptor was calculated by software after the raw data of the example compounds were collected, so as to evaluate the agonist activity of the example compounds on human calcium-sensing receptor.

3.1.3 Data Processing:

HTRF signal was read by an EnVision detector with an excitation wavelength of 320 nm and emission wavelengths of 620 nm and 665 nm. The signal ratio (665 nm/620 nm×10,000) was calculated and fitted non-linearly to the sample concentration in GraphPad Prism 6 using a four-parameter equation to give $EC_{50}$ values of the test example compounds 1-38. The specific values are shown in Table 2 below.

TABLE 2

In vitro agonist activity of compounds 1-38 on calcium-sensing receptor

| Compound | Sequence | SEQ ID NO: | $EC_{50}$ for calcium-sensing receptor (μM) |
|---|---|---|---|
| 1 | Ac-c(C)-(D-Phg)-r-r-r-a-r-$NH_2$ | 1 | 15.71 |
| 2 | Ac-c(C)-[D-Phe(2-Cl)]-r-r-r-a-r-$NH_2$ | 2 | 6.76 |
| 3 | Ac-c(C)-[D-Phe(4-$CH_3$)]-r-r-r-a-r-$NH_2$ | 3 | 15.28 |
| 4 | Ac-c(C)-(D-Tyr)-r-r-r-a-r-$NH_2$ | 4 | 6.92 |
| 5 | Ac-c(C)-(D-Trp)-r-r-r-a-r-$NH_2$ | 5 | 1.14 |
| 6 | Ac-c(C)-s-r-r-r-s-r-$NH_2$ | 6 | 11.56 |
| 7 | Ac-c(C)-h-r-r-r-G-r-$NH_2$ | 7 | 18.60 |
| 8 | Ac-c(C)-s-r-r-r-G-r-$NH_2$ | 8 | 14.32 |
| 9 | Ac-c(C)-w-r-r-r-G-r-$NH_2$ | 9 | 3.16 |
| 10 | Ac-c(C)-h-r-r-r-s-r-$NH_2$ | 10 | 3.52 |
| 11 | Ac-c(C)-r-r-(D-Phg)-r-a-r-$NH_2$ | 11 | 15.71 |
| 12 | Ac-c(C)-r-r-[D-Phe(4-$CH_3$)]-r-a-r-$NH_2$ | 12 | 1.28 |
| 13 | Ac-c(C)-r-r-(D-2-Thi)-r-a-r-$NH_2$ | 13 | 1.21 |
| 14 | Ac-c(C)-r-r-[D-Phe(4-$NO_2$)]-r-a-r-$NH_2$ | 14 | 4.33 |
| 15 | Ac-c(C)-r-r-(D-2-NaI)-r-a-r-$NH_2$ | 15 | 5.59 |
| 16 | Ac-c(C)-r-r-(D-hPhe)-r-a-r-$NH_2$ | 16 | 2.37 |
| 17 | Ac-c(C)-r-r-(D-Abu)-r-a-r-$NH_2$ | 17 | 6.28 |
| 18 | Ac-c(C)-r-r-(D-Tle)-r-a-r-$NH_2$ | 18 | 13.37 |
| 19 | Ac-c(C)-r-r-(D-hLeu)-r-a-r-$NH_2$ | 19 | 2.05 |
| 20 | Ac-c(C)-r-r-(D-Chg)-r-a-r-$NH_2$ | 20 | 7.53 |
| 21 | Ac-c(C)-r-r-(D-Cha)-r-a-r-$NH_2$ | 21 | 5.59 |
| 22 | Ac-c(C)-r-r-s-r-G-r-$NH_2$ | 22 | 15.41 |
| 23 | Ac-c(C)-r-r-q-r-G-r-$NH_2$ | 23 | 30.40 |
| 24 | Ac-c(C)-r-r-y-r-a-r-$NH_2$ | 24 | 2.03 |
| 25 | Ac-c(C)-r-r-s-r-s-r-$NH_2$ | 25 | 10.08 |
| 26 | Ac-c(C)-r-r-q-r-s-r-$NH_2$ | 26 | 9.24 |
| 27 | Ac-c(C)-r-r-h-r-s-r-$NH_2$ | 27 | 10.81 |

TABLE 2-continued

In vitro agonist activity of compounds 1-38 on calcium-sensing receptor

| Compound | Sequence | SEQ ID NO: | $EC_{50}$ for calcium-sensing receptor (μM) |
|---|---|---|---|
| 28 | Ac-c(C)-r-r-h-r-G-r-$NH_2$ | 28 | 21.50 |
| 29 | Ac-c(C)-r-r-v-r-s-r-$NH_2$ | 29 | 9.80 |
| 30 | Ac-c(C)-r-r-v-r-G-r-$NH_2$ | 30 | 19.57 |
| 31 | Ac-c(C)-r-r-(D-Abu)-r-s-r-$NH_2$ | 31 | 5.93 |
| 32 | Ac-c(C)-r-r-(D-Abu)-r-G-r-$NH_2$ | 32 | 13.09 |
| 33 | Ac-c(C)-r-r-(D-hLeu)-r-s-r-$NH_2$ | 33 | 5.03 |
| 34 | Ac-c(C)-r-r-(D-hLeu)-r-G-r-$NH_2$ | 34 | 12.19 |
| 35 | Ac-c(C)-r-r-(D-Chg)-r-s-r-$NH_2$ | 35 | 12.94 |
| 36 | Ac-c(C)-r-r-(D-Chg)-r-G-r-$NH_2$ | 36 | 17.95 |
| 37 | Ac-c(C)-r-r-(D-Tle)-r-s-r-$NH_2$ | 37 | 15.45 |
| 38 | Ac-c(C)-r-r-(D-Tle)-r-G-r-$NH_2$ | 38 | 18.73 |
| Etelcalcetide | Ac-c(C)-a-r-r-r-a-r-$NH_2$ | 40 | 6.78 |
| Etelcalcetide analogue | Ac-c(C)-r-r-a-r-a-r-$NH_2$ | 41 | 6.74 |

Positive controls etelcalcetide and the etelcalcetide analogue in the above table were prepared according to the method disclosed in Patent No. WO2011014707.

A considerable portion of the example compounds disclosed herein demonstrated excellent in vitro efficacy, corresponding to $EC_{50}$ values less than 10 μM in the in vitro agonist activity evaluation on human calcium-sensing receptor.

3.2 Evaluation of In Vitro Activity of Compounds 1-38 to Induce Histamine Release in Rat Peritoneal Mast Cells 3.2.1 Objective: To Evaluate the In Vitro Activity of the Test Compounds 1-38 to Induce Histamine Release in Rat Peritoneal Mast Cells 3.2.2 Procedures and Data Processing:

To evaluate the in vitro histamine release levels induced by some of the test example compounds, rat peritoneal mast cells were collected by lavaging rat peritoneum with a lavage buffer (cold HBSS+25 mM HEPES containing heparin 5 U/mL, pH 7.4). After collection, the cells were centrifuged, and the lavage buffer was discarded. The cells were resuspended and washed twice with a stimulation buffer (HBSS+25 mM HEPES+1 mM $CaCl_2$), pH 7.4). The cells were plated at a density of $10^5$ cell/well (200 μL/well) and incubated at 37° C. for 15 min with positive control compound 48/80 (final concentration: 4 μg/mL), test example compounds (final concentration: 10 μM) or vehicle control. The cells were centrifuged, and cell supernatant was collected and tested for histamine concentration according to LDN Histamine ELISA kit (BAE-1000) instructions. Specific data are shown in Table 3 below.

TABLE 3

Histamine release levels in vitro induced by some of the compounds disclosed herein

| Example | Relative fold of histamine release in vitro |
|---|---|
| PBS buffer | 1.00 |
| Compound 48/80 | 8.78 |
| 1 | 1.50 |
| 2 | 4.96 |
| 4 | 3.94 |
| 5 | 4.13 |
| 6 | 1.65 |
| 7 | 2.24 |
| 8 | 1.50 |
| 10 | 3.66 |
| 11 | 1.11 |
| 12 | 2.81 |
| 13 | 2.38 |
| 16 | 2.94 |
| 17 | 0.97 |
| 18 | 1.24 |
| 19 | 2.07 |
| 20 | 2.33 |
| 21 | 3.42 |
| 22 | 1.63 |
| 24 | 3.18 |
| 25 | 1.65 |
| 26 | 1.73 |
| 27 | 2.23 |
| 29 | 0.99 |
| 30 | 1.51 |
| 31 | 1.29 |
| 32 | 1.41 |
| 33 | 2.50 |
| 34 | 2.28 |

TABLE 3-continued

Histamine release levels in vitro induced by some of the compounds disclosed herein

| Example | Relative fold of histamine release in vitro |
|---|---|
| 35 | 2.06 |
| 37 | 2.23 |
| Etelcalcetide | 1.70 |

A considerable portion of the compounds disclosed herein did not significantly induce histamine release in rat peritoneal mast cells in vitro, in particular at a relative histamine release fold less than 1.50 relative to PBS buffer. Surprisingly, amino acid substitutions in some compounds resulted in a reduction in histamine release levels in rat peritoneal mast cells in vitro relative to the etelcalcetide, e.g., examples 17, 29, 31 and 32.

3.3 Evaluation of Hemolytic Effect of Some of the Compounds Disclosed Herein on Human Red Blood Cells In Vitro 3.3.1 Objective: To Evaluate the Hemolytic Effect of Some of the Compounds Disclosed Herein on Human Red Blood Cells In Vitro.

3.3.2 Procedures and Data Processing:

To evaluate the hemolytic effect of the compounds disclosed herein on red blood cells in vitro, human whole blood (100 μL) was taken and mixed with a phosphate buffer. The mixture was centrifuged at 4° C. for 10 min and the supernatant was discarded. The red blood cells were resuspended in PBS buffer (900 μL) and centrifuged at 4° C. for 10 min with the supernatant discarded, and the procedures above were repeated once. The test example compounds were dissolved in 1×PBS buffer to a final concentration of 100 μg/mL. The red blood cells were resuspended in solutions of various test example compounds, an octylphenoxy poly(ethyleneoxy)ethanol-100 solution or PBS buffer, and incubated at 37° C. for 1 h. After incubation, the cells were centrifuged at 4° C. for 10 min and the supernatant (100 μL) was pipetted and transferred to a 96-well plate. The absorbance at 540 nm was detected for evaluating the hemolytic effect of the test example compounds on red blood cells in vitro.

3.3.3 Results

At a concentration of 100 μg/mL, no significant hemolytic effect on red blood cells was observed for compounds 12, 13, 17, 19, 29 and 31 of the present disclosure, while the octylphenoxy poly(ethyleneoxy)ethanol-100 solution demonstrated a significant hemolytic effect on red blood cells under the experimental conditions, as shown in FIG. 1.

3.4 Evaluation of In Vivo Efficacy of Some of the Compounds Disclosed Herein in a Normal Rat Model after a Single Dose 3.4.1 Objective: To Evaluate the Efficacy of the Test Compounds in Reducing Plasma Parathyroid Hormone Levels after a Single Dose in a Normal Rat Model.

3.4.2 Procedures and Data Processing:

SPF normal adult rats (Sprague Dawley, or SD) with weight of 250-350 g were fed with normal diet in an animal room for 7 days. Rats were randomized into groups of 6, half female and half male, and numbered. One day before the start of treatment, 540 μL of blood was collected from each rat, and the plasma parathyroid hormone level and the serum calcium concentration were measured as baseline. The plasma was separated by K2-EDTA anticoagulation. Blood was collected through jugular vein and preserved on ice after collection. The whole blood was centrifuged at 6,800 rpm for 6 minutes at 2-8° C. The supernatant, i.e., the plasma, was collected and preserved at 2-8° C. For serum separation, blood was collected through jugular vein, let stand at room temperature for 1 h, and centrifuged at room temperature at 3,500 rpm for 10 min. The supernatant, i.e., the serum, was collected and preserved at room temperature. The animals were fasted overnight with free access to water the day before treatment. The day after blood sampling, example compounds 13, 17, 31 and etelcalcetide (AMG-416) were dissolved in a phosphate buffered saline (PBS, Gibco). The rats were intravenously administered with example compounds 13, 17, 31 or etelcalcetide 3 mg/kg or an equal volume of PBS buffer. Subsequently, blood samples were collected as per the following procedures for measuring the parameters. 100 μL of blood was collected at 1 h, 2 h and 4 h post-dose, and the plasma was separated according to the procedures above. The plasma parathyroid hormone levels were measured using the Rat Intact PTH ELISA Kit (Quidel—Immunotopics, Cat. #: 60-2500; ELISA: Enzyme-linked immunosorbent assay) according to the kit instructions. The detailed procedures are as follows: using the streptavidin-preplated reaction strips provided in the kit, 25 μL of reference standard, control or plasma samples were added to the wells. Biotinylated rat parathyroid hormone antibody and rat parathyroid hormone/HRP binding antibody were mixed at a ratio of 1:1, and 100 μL of the mixed solution was added to each well. The reaction strip was sealed with a sealing film, wrapped with an aluminum foil for storage in dark, and shaken on a horizontal shaker at room temperature for 3 h at a rotation speed of 220 rpm. The solutions in the wells were discarded. 350 μL of cleaning working solution was added to the wells for washing and then discarded; 5 washes were performed with the same procedures. Finally the wells were dried. To each well was added 150 μL of horseradish peroxidase ELISA substrate. The reaction strip was sealed with a sealing film, wrapped with an aluminum foil for storage in dark, and shaken on a horizontal shaker at room temperature for 30 min at a rotation speed of 180-220 rpm. 100 μL of ELISA terminating solution was added to each well, and the strip was shaken at 180-220 rpm for 1 min on a horizontal shaker at room temperature. The absorbance at 450 nm in each well was detected within 10 min after the addition of the ELISA terminating solution, while the absorbance at 620 nm was subtracted as background. A mixture of horseradish peroxidase ELISA substrate 150 μL and ELISA terminating solution 100 μL was used as the blank control in the absorbance detection. A standard curve according to the absorbance of the reference standard was plotted, and the actual plasma parathyroid hormone concentration was calculated according to the absorbance of other samples and the standard curve. The determination of the serum calcium concentration was conducted according to the procedures of the relevant kit.

3.4.3 Results

Figure 2:
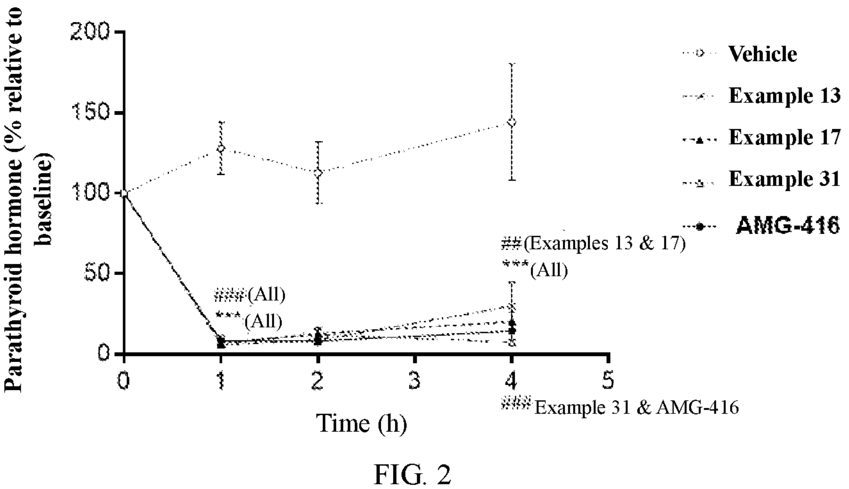
FIG. 2 shows the efficacy of 3 mg/kg of example compounds 13, 17, 31 and etelcalcetide (AMG-416) in reducing parathyroid hormone level in normal rats.
Figure 3:
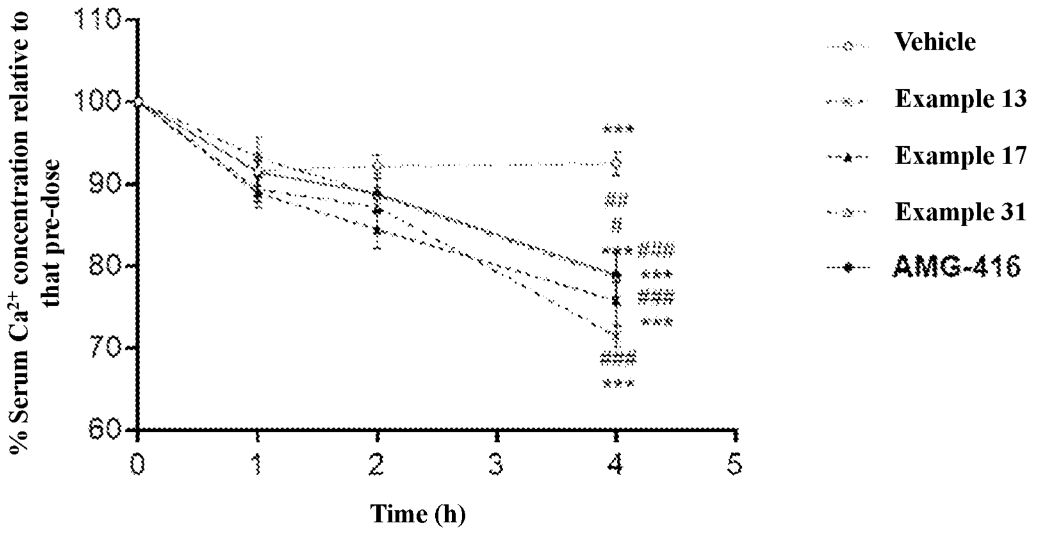
FIG. 3 shows the efficacy of 3 mg/kg of example compounds 13, 17, 31 and etelcalcetide (AMG-416) in reducing serum calcium level in normal rats.

Test compounds 13, 17 and 31 completely reduced the plasma parathyroid hormone level in normal rats within 4 h at a dose of 3 mg/kg, and a corresponding reduction in serum calcium level was also observed, as shown in FIGS. 2 and 3.

3.5 Evaluation of In Vivo Efficacy of Some of the Compounds Disclosed Herein in a 5/6 Nephrectomized Rat Model after Continuous Administration 3.5.1 Objective: to evaluate the efficacy of some of the compounds disclosed herein in reducing plasma parathyroid hormone level and serum calcium level after continuous administration in a 5/6 nephrectomized rat model.

3.5.2 Procedures and Data Processing:

The rats were adapted. After anesthesia, ⅔ of the left kidney was surgically resected, and after 1 week of recovery, the right kidney was resected to establish the 5/6 nephrectomized rat model. After the second resection, the animals were normally fed for 2 weeks, tested for creatinine (CREA) and plasma parathyroid hormone level, and randomized as per the parathyroid hormone level into 4 groups of 10, including normal saline group, compound 17—low dose group, compound 17—high dose group and etelcalcetide group. After randomization, the normal saline group, compound 17—low dose group, compound 17—high dose group and etelcalcetide group were respectively administered with 1 dose of normal saline, 1 mg/kg of compound 17, 2 mg/kg of compound 17 and 1 mg/kg of etelcalcetide through the tail vein daily for 28 days. During the treatment period, parameters such as animal weight, plasma parathyroid hormone level and serum calcium were detected. The first day of treatment was taken as day 1.

Figure 4A:
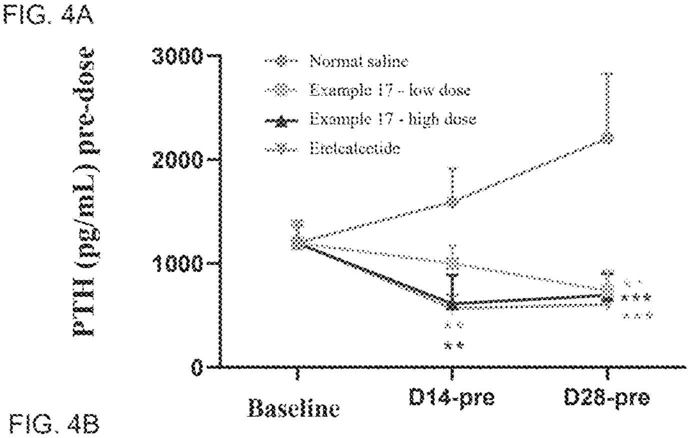
FIGS. 4A-C show the efficacy of example compound 17 and etelcalcetide (AMG-416) in reducing parathyroid hormone level in 5/6 nephrectomized rats.
Figure 4B:
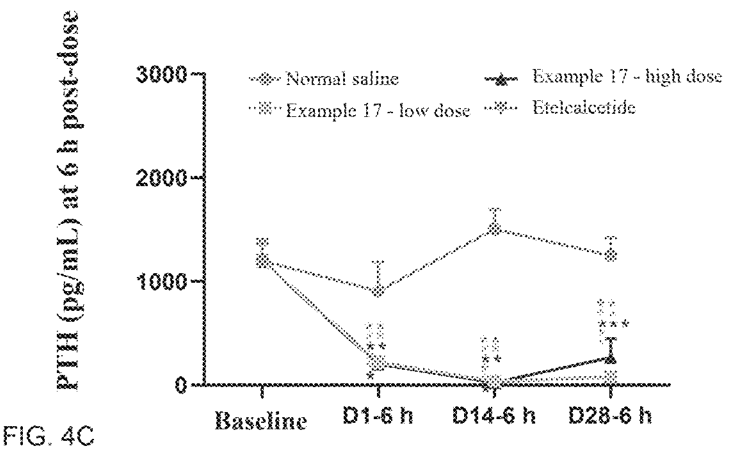
Figure 4C:
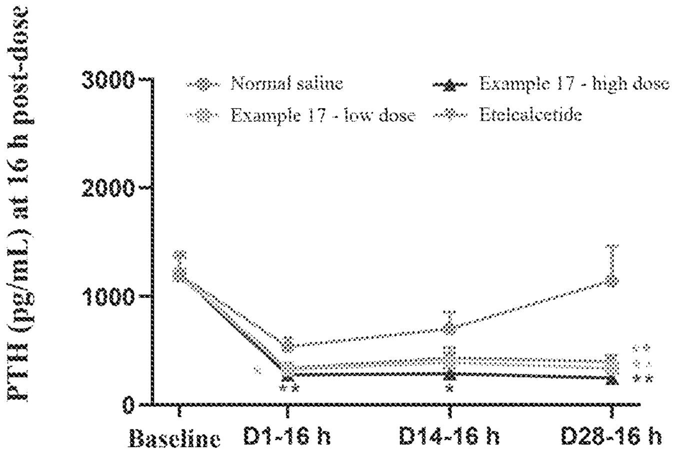
Figure 5:
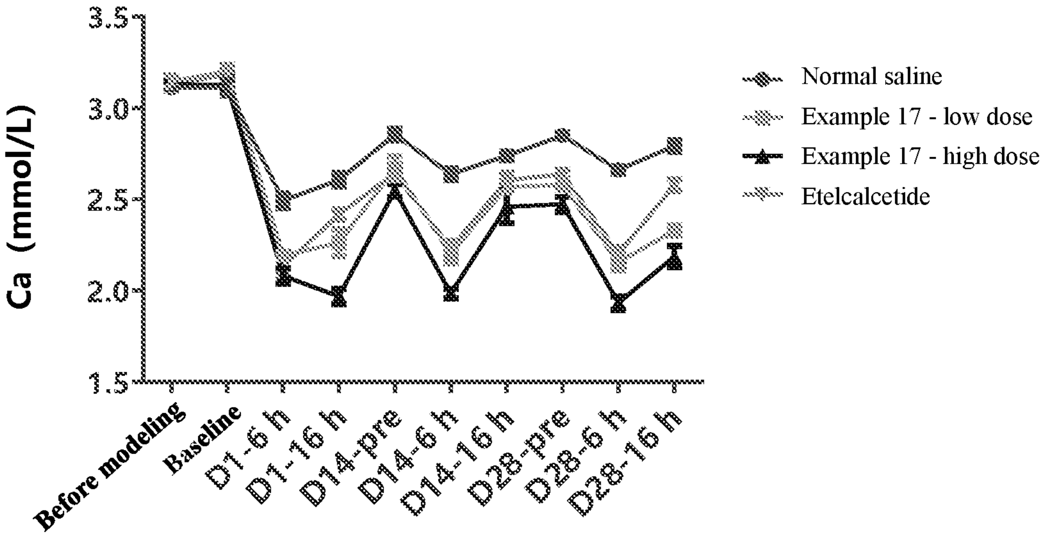
FIG. 5 shows the efficacy of example compound 17 and etelcalcetide (AMG-416) in reducing serum calcium level in 5/6 nephrectomized rats.

3.5.3 Results and Conclusions:

Compared with the normal saline group, the example compound 17 1 mg/kg and 2 mg/kg reduced the plasma parathyroid hormone level in rats in a dose dependent manner. The parathyroid hormone level was reduced to an extremely low level in various treatment groups at 6 h post-dose on days 1, 14 and 28, and the parathyroid hormone reduction was greater than 90% since day 14. During the treatment period, compound 17 1 mg/kg suppressed the plasma parathyroid hormone level at 6 h and 16 h post-dose by a slightly superior or comparable magnitude to that of etelcalcetide at the same dose (FIG. 4). Serum calcium reduction is a mechanism-related effect for drugs of the type. In this study, after administration on days 1, 14 and 28, both compound 17 and etelcalcetide induced reversible serum calcium reduction. There was no significant difference in the minimum of serum calcium on days 14 and 28 compared to day 1 in various treatment group, suggesting that the extent of serum calcium reduction induced by compound 17 and etelcalcetide did not increase with the period of treatment. The maximal reduction in serum calcium induced by compound 17 was comparable to etelcalcetide at the same dose on days 1, 14 and 28, suggesting that compound 17 has comparable serum calcium-reducing activity to etelcalcetide (FIG. 5). Notably, the persistence of compound 17 to reduce serum calcium levels at day 28 was superior and significantly different as compared to etelcalcetide at the same dose.

The invention claimed is:

1. A compound consisting of Ac-c(C)-r-r-(D-Abu)-r-a-r-$NH_2$ (SEQ ID NO: 17) or a pharmaceutically acceptable salt thereof.

2. A pharmaceutical composition comprising the compound or the pharmaceutically acceptable salt thereof according to claim 1.

3. A method of treating a disease associated with excessive parathyroid hormone levels in a subject in need thereof, wherein the method comprises administering to the subject a therapeutically effective amount of the compound, or the pharmaceutically acceptable salt thereof according to claim 1, or the pharmaceutical composition according to claim 2.

4. The method according to claim 3, wherein the disease associated with excessive parathyroid hormone levels is hyperparathyroidism.

5. The method according to claim 4, wherein the hyperparathyroidism is a secondary hyperparathyroidism in a subject with chronic kidney disease.

* * * * *

SEQUENCE LISTING

```
<160> NUMBER OF SEQ ID NOS: 41

<210> SEQ ID NO 1
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: Xaa = D-Phg
<220> FEATURE:
<221> NAME/KEY: VARIANT
<222> LOCATION: (3)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 1

Xaa Xaa Xaa Xaa Xaa Xaa Xaa
1               5
```

<210> SEQ ID NO 2
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: Xaa = D-Phe(2-Cl)
<220> FEATURE:
<221> NAME/KEY: VARIANT
<222> LOCATION: (3)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 2

```
Xaa Xaa Xaa Xaa Xaa Xaa Xaa
1               5
```

<210> SEQ ID NO 3
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: Xaa = D-Phe(4-CH3)
<220> FEATURE:
<221> NAME/KEY: VARIANT
<222> LOCATION: (3)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)

<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 3

Xaa Xaa Xaa Xaa Xaa Xaa Xaa
1               5

<210> SEQ ID NO 4
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: Xaa = D-Tyr
<220> FEATURE:
<221> NAME/KEY: VARIANT
<222> LOCATION: (3)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 4

Xaa Xaa Xaa Xaa Xaa Xaa Xaa
1               5

<210> SEQ ID NO 5
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: D-Trp -continued
<220> FEATURE:
<221> NAME/KEY: VARIANT
<222> LOCATION: (3)..(5)
<223> OTHER INFORMATION: D-Arg
<220> FEATURE:
<221> NAME/KEY: VARIANT
<222> LOCATION: (6)..(6)
<223> OTHER INFORMATION: D-Ala
<220> FEATURE:
<221> NAME/KEY: VARIANT
<222> LOCATION: (7)..(7)
<223> OTHER INFORMATION: D-Arg
<220> FEATURE:
<221> NAME/KEY: MOD_RES
<222> LOCATION: (7)..(7)
<223> OTHER INFORMATION: C-terminally amidated

<400> SEQUENCE: 5

Xaa Xaa Xaa Xaa Xaa Xaa Xaa
1 5

<210> SEQ ID NO 6
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: D-Ser
<220> FEATURE:
<221> NAME/KEY: VARIANT
<222> LOCATION: (3)..(5)
<223> OTHER INFORMATION: D-Arg
<220> FEATURE:
<221> NAME/KEY: VARIANT
<222> LOCATION: (6)..(6)
<223> OTHER INFORMATION: D-Ser
<220> FEATURE:
<221> NAME/KEY: VARIANT
<222> LOCATION: (7)..(7)
<223> OTHER INFORMATION: D-Arg
<220> FEATURE:
<221> NAME/KEY: MOD_RES
<222> LOCATION: (7)..(7)
<223> OTHER INFORMATION: C-terminally amidated

<400> SEQUENCE: 6

Xaa Xaa Xaa Xaa Xaa Xaa Xaa
1 5

<210> SEQ ID NO 7
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: D-Cys
<220> FEATURE:

<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: D-His
<220> FEATURE:
<221> NAME/KEY: VARIANT
<222> LOCATION: (3)..(5)
<223> OTHER INFORMATION: D-Arg
<220> FEATURE:
<221> NAME/KEY: VARIANT
<222> LOCATION: (7)..(7)
<223> OTHER INFORMATION: D-Arg
<220> FEATURE:
<221> NAME/KEY: MOD_RES
<222> LOCATION: (7)..(7)
<223> OTHER INFORMATION: C-terminally amidated

<400> SEQUENCE: 7

Xaa Xaa Xaa Xaa Xaa Gly Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: D-Ser
<220> FEATURE:
<221> NAME/KEY: VARIANT
<222> LOCATION: (3)..(5)
<223> OTHER INFORMATION: D-Arg
<220> FEATURE:
<221> NAME/KEY: VARIANT
<222> LOCATION: (7)..(7)
<223> OTHER INFORMATION: D-Arg
<220> FEATURE:
<221> NAME/KEY: MOD_RES
<222> LOCATION: (7)..(7)
<223> OTHER INFORMATION: C-terminally amidated

<400> SEQUENCE: 8

Xaa Xaa Xaa Xaa Xaa Gly Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: D-Trp
<220> FEATURE:
<221> NAME/KEY: VARIANT
<222> LOCATION: (3)..(5)
<223> OTHER INFORMATION: D-Arg
<220> FEATURE:
<221> NAME/KEY: VARIANT
<222> LOCATION: (7)..(7)
<223> OTHER INFORMATION: D-Arg
<220> FEATURE:
<221> NAME/KEY: MOD_RES
<222> LOCATION: (7)..(7)
<223> OTHER INFORMATION: C-terminally amidated

<400> SEQUENCE: 9

Xaa Xaa Xaa Xaa Xaa Gly Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: D-His
<220> FEATURE:
<221> NAME/KEY: VARIANT
<222> LOCATION: (3)..(5)
<223> OTHER INFORMATION: D-Arg
<220> FEATURE:
<221> NAME/KEY: VARIANT
<222> LOCATION: (6)..(6)
<223> OTHER INFORMATION: D-Ser
<220> FEATURE:
<221> NAME/KEY: VARIANT
<222> LOCATION: (7)..(7)
<223> OTHER INFORMATION: D-Arg
<220> FEATURE:
<221> NAME/KEY: MOD_RES
<222> LOCATION: (7)..(7)
<223> OTHER INFORMATION: C-terminally amidated

<400> SEQUENCE: 10

Xaa Xaa Xaa Xaa Xaa Xaa Xaa
1               5

<210> SEQ ID NO 11

<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Phg
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 11

```
Xaa Xaa Xaa Xaa Xaa Xaa Xaa
1               5
```

<210> SEQ ID NO 12
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Phe(4-CH3)
<220> FEATURE:
<221> NAME/KEY: VARIANT
<222> LOCATION: (5)..(5)
<223> OTHER INFORMATION: Xaa = D-Arg
<220> FEATURE:

<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 12

Xaa Xaa Xaa Xaa Xaa Xaa Xaa
1 5

<210> SEQ ID NO 13
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-2-Thi
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 13

Xaa Xaa Xaa Xaa Xaa Xaa Xaa
1 5

<210> SEQ ID NO 14
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES

```
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = Phe(4-NO2)
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 14

Xaa Xaa Xaa Xaa Xaa Xaa Xaa
1               5


<210> SEQ ID NO 15
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-2-NaI
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated
```

<400> SEQUENCE: 15

Xaa Xaa Xaa Xaa Xaa Xaa Xaa
1 5

<210> SEQ ID NO 16
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-hPhe
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 16

Xaa Xaa Xaa Xaa Xaa Xaa Xaa
1 5

<210> SEQ ID NO 17
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = Arg
<220> FEATURE:

```
<221> NAME/KEY: VARIANT
<222> LOCATION: (4)..(4)
<223> OTHER INFORMATION: Xaa = D-Abu
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 17

Xaa Xaa Xaa Xaa Xaa Xaa Xaa
1               5


<210> SEQ ID NO 18
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Tle
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 18

Xaa Xaa Xaa Xaa Xaa Xaa Xaa
1               5


<210> SEQ ID NO 19
<211> LENGTH: 7
<212> TYPE: PRT
<213> ORGANISM: Artificial Sequence
```

<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-hLeu
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 19

Xaa Xaa Xaa Xaa Xaa Xaa Xaa
1               5

<210> SEQ ID NO 20
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Chg
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 20

Xaa Xaa Xaa Xaa Xaa Xaa Xaa
1               5

<210> SEQ ID NO 21
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Cha
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 21

Xaa Xaa Xaa Xaa Xaa Xaa Xaa
1               5

<210> SEQ ID NO 22
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:

<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Ser
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 22

Xaa Xaa Xaa Xaa Xaa Gly Xaa
1               5

<210> SEQ ID NO 23
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Gln
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 23

Xaa Xaa Xaa Xaa Xaa Gly Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Tyr
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 24

Xaa Xaa Xaa Xaa Xaa Xaa Xaa
1               5

<210> SEQ ID NO 25
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Ser
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ser
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 25

Xaa Xaa Xaa Xaa Xaa Xaa Xaa
1               5

<210> SEQ ID NO 26
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Gln
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ser
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 26

Xaa Xaa Xaa Xaa Xaa Xaa Xaa
1               5

<210> SEQ ID NO 27
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:

<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-His
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ser
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 27

Xaa Xaa Xaa Xaa Xaa Xaa Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-His
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 28

Xaa Xaa Xaa Xaa Xaa Gly Xaa
1               5

<210> SEQ ID NO 29
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Val
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ser
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 29

Xaa Xaa Xaa Xaa Xaa Xaa Xaa
1               5

<210> SEQ ID NO 30
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Val
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 30

Xaa Xaa Xaa Xaa Xaa Gly Xaa
1               5

<210> SEQ ID NO 31
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Abu
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ser
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 31

Xaa Xaa Xaa Xaa Xaa Xaa Xaa
1               5

<210> SEQ ID NO 32
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:

<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Abu
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 32

Xaa Xaa Xaa Xaa Xaa Gly Xaa
1               5

<210> SEQ ID NO 33
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-hLeu
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ser
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 33

Xaa Xaa Xaa Xaa Xaa Xaa Xaa
1               5

<210> SEQ ID NO 34
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-hLeu
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 34

Xaa Xaa Xaa Xaa Xaa Gly Xaa
1               5

<210> SEQ ID NO 35
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Chg
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ser
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 35

Xaa Xaa Xaa Xaa Xaa Xaa Xaa
1               5

<210> SEQ ID NO 36
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Chg
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 36

Xaa Xaa Xaa Xaa Xaa Gly Xaa
1               5

<210> SEQ ID NO 37
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:

<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Tle
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ser
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 37

Xaa Xaa Xaa Xaa Xaa Xaa Xaa
1               5

<210> SEQ ID NO 38
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Tle
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 38

Xaa Xaa Xaa Xaa Xaa Gly Xaa
1               5

<210> SEQ ID NO 39
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: VARIANT
<222> LOCATION: (2)..(2)
<223> OTHER INFORMATION: Xaa = D-Phg, D-Phe(4-CH3), D-Phe(2-Cl), D-Tyr, D-Trp, D-Ser, D-Arg, D-Trp or D-His
<220> FEATURE:
<221> NAME/KEY: VARIANT
<222> LOCATION: (3)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Arg, D-Phg, D-Phe(4-CH3), D-2-Thi, D-Phe(4-NO2), D-2-NaI, D-hPhe, D-Abu, D-Tle, D-hLeu, D-Cha, D-Ser, D-Gln, D-Tyr, D-Ile, D-Ser, D-His, D-Val or D-Chg
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala, D-Abu, D-Ser or Gly
<220> FEATURE:
<221> NAME/KEY: MOD_RES
<222> LOCATION: (7)..(7)
<223> OTHER INFORMATION: C-terminally amidated
<220> FEATURE:
<221> NAME/KEY: VARIANT
<222> LOCATION: (7)..(7)
<223> OTHER INFORMATION: Xaa = D-Arg

<400> SEQUENCE: 39

Xaa Xaa Xaa Xaa Xaa Xaa Xaa
1 5

<210> SEQ ID NO 40
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(2)
<223> OTHER INFORMATION: Xaa = D-Ala
<220> FEATURE:
<221> NAME/KEY: VARIANT
<222> LOCATION: (3)..(5)
<223> OTHER INFORMATION: Xaa = D-Arg
<220> FEATURE:

-continued

```
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 40

Xaa Xaa Xaa Xaa Xaa Xaa Xaa
1               5


<210> SEQ ID NO 41
<211> LENGTH: 7
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminally acetylated
<220> FEATURE:
<221> NAME/KEY: DISULFID
<222> LOCATION: (1)..(1)
<223> OTHER INFORMATION: Cys-Cys disulfide bond formed with L-Cys
<220> FEATURE:
<221> NAME/KEY: VARIANT
<222> LOCATION: (2)..(3)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Ala
<220> FEATURE:
<221> NAME/KEY: VARIANT
<222> LOCATION: (5)..(5)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: VARIANT
<222> LOCATION: (7)..(7)
<223> OTHER INFORMATION: Xaa = D-Arg
<220> FEATURE:
<221> NAME/KEY: MOD_RES
<222> LOCATION: (7)..(7)
<223> OTHER INFORMATION: C-terminally amidated

<400> SEQUENCE: 41

Xaa Xaa Xaa Xaa Xaa Xaa Xaa
1               5
```